United States Patent
Shakespeare et al.

(10) Patent No.: US 7,961,319 B2
(45) Date of Patent: Jun. 14, 2011

(54) METHOD AND APPARATUS FOR MEASURING COLOR OF A MOVING WEB

(75) Inventors: Tarja Shakespeare, Hiltulanlahti (FI); Mikko Toivonen, Pirkkala (FI); Mark Peczkis, Richmond Hill (CA)

(73) Assignee: Metso Automation Oy, Helsinki (FI)

( * ) Notice: Subject to any disclaimer, the term of this patent is extended or adjusted under 35 U.S.C. 154(b) by 198 days.

(21) Appl. No.: 11/794,117

(22) PCT Filed: Dec. 22, 2005

(86) PCT No.: PCT/FI2005/050478
§ 371 (c)(1),
(2), (4) Date: Jun. 18, 2008

(87) PCT Pub. No.: WO2006/070070
PCT Pub. Date: Jul. 6, 2006

(65) Prior Publication Data
US 2009/0141265 A1    Jun. 4, 2009

(30) Foreign Application Priority Data
Dec. 31, 2004  (FI) ..................................... 20045512

(51) Int. Cl.
*G01J 3/50*  (2006.01)
*G01N 21/86*  (2006.01)
(52) U.S. Cl. .......................... 356/402; 356/73; 356/429
(58) Field of Classification Search .................... 356/73, 356/402
See application file for complete search history.

(56) References Cited

U.S. PATENT DOCUMENTS

| | | | |
|---|---|---|---|
| 4,243,319 | A | 1/1981 | Lodzinski |
| 4,944,594 | A | 7/1990 | Burk |
| 5,793,486 | A | 8/1998 | Gordon et al. |
| 2004/0021869 | A1 | 2/2004 | Shakespeare et al. |

*Primary Examiner* — F. L Evans
(74) *Attorney, Agent, or Firm* — Oliff & Berridge, PLC

(57) ABSTRACT

A method and an apparatus for measuring color of a moving web. The web is measured by reflectance measurement and transmittance measurement, wherein the reflectance measurement is carried out by illuminating a surface of the web in a measuring area, where on the other side of the web at the measuring area resides a solidly attached backing element and measuring the radiation reflected from the web. The transmittance measurement is carried out by illuminating the web and measuring the radiation transmitted through the web. The radiation measured in the transmittance measurement is transmitted through the backing element.

23 Claims, 6 Drawing Sheets

METHOD AND APPARATUS FOR MEASURING COLOR OF A MOVING WEB

FIELD OF THE INVENTION

The invention relates to a method for measuring color of a moving web. The invention also relates to an apparatus for implementing the above-mentioned method.

BACKGROUND OF THE INVENTION

In a modern paper mill, the paper making process is monitored continuously. Paper is produced from pulp slurry as a continuous web that is reeled at the end of the process. There are several measuring points in the process for monitoring the process equipment as well as the raw material, pulp in the wet end of the paper machine and the end product, that is, paper in the dry end of the machine.

Paper measurements are made both in the paper laboratory of the mill and on-line, during the paper making process, when the paper is moving continuously in the machine. The measuring unit in the paper machine is usually set up in an open draw of the travelling path of the web, consisting of a measuring beam extending across the web, in its CD-direction (Cross Direction). In the measuring beam, there are mounted two sensor platforms, one adjacent to each of the web surfaces, where the measuring sensors are located so that the two heads of each sensor are facing each other and located on the opposite sides of the web. The platforms traverse the web back and fourth in its cross direction, while the web is moving. In a modern paper machine, the paper travels in a speed of 1600-2200 meters/minute. The sensor mounted on a platform is moving across the web in a speed of about 30-60 meters/minute. So the sensors travel across the web along a zig-zag travelling path. Also measuring units, set up in such a way that only certain position in the CD-direction of the web is measured, are being used. In this arrangement, the sensor platforms are set up at a fixed point in the CD-direction of the web.

Optical properties of paper, such as opacity, color, whiteness, brightness and fluorescence index are measured by illuminating the web and detecting the light reflected from and optionally also transmitted through the paper. In many paper products, like books or newspapers, the user sees a stack of multiple paper sheets rather than a single layer of paper. If paper is not totally opaque, color and other optical properties of the stack are different than those of a single sheet. This is because some of the light reaching the observer's eye is reflected from the sheets placed below the top one. Typically, at a paper mill's laboratory, measurements of optical properties of paper are made against a backing of an opaque stack of the same paper of multiple paper sheets. This is to eliminate the effect of the incomplete opacity of a single sheet on the measurements. When measuring a continuously moving paper web on-line, it is not possible to form a stack of paper sheets as required and thus the method used at laboratory cannot be used. Close match between on-line measurements and off-line measurements, e.g. laboratory measurement results is a basic requirement in nowadays papermaking. Thus, the on-line measurement needs to have means for compensation of the effects of incomplete opacity on the results.

Several methods for measuring opacity compensated paper web color on-line have been suggested. These methods measure the single thickness of the web and aim at producing a measuring result that is comparable with the laboratory measurements of a stack of paper. One possibility is to measure the reflectance of the web against a suitable opaque backing resembling the color and reflectivity of the measured paper. An effect of the backing on the measured color is similar to that of a stack of paper. However, this method is not sufficient: the properties of the backing are never the same as that of the measured web. Moreover, the change of paper color requires a change of backing.

Another method is to use two essentially different backings for the measurement, for example one of them being a black backing, which is highly absorptive and the other being a white backing that is highly reflective. The reflectance of the paper against both of these backings is measured. From these measurements it is possible, for example by using the Kubelka-Munk theory, to calculate the influence of the sheet transmittance on the reflectance of the paper stack and deduce the reflectance both for a single sheet and a stack of paper sheets. The problem with this measurement is that the measurements against different backings are made at different times, one after the other, because the method requires the changing of the backings between the measurements. This change can only be done by relatively slow mechanical means. As the web and possibly also the sensor is moving, these measurements against white and black backings are made from different parts of the paper, and this decreases the usability, quality and speed of the color measurement. Another problem with this arrangement is that the sensor construction includes moving parts for changing the backings that need maintenance.

A modification of this method is presented in U.S. Pat. No. 4,944,594, where instead of using two different backings, an optical gating means is placed adjacent the paper to provide a backing for the reflectance measurement. The optical gating has two operating states, a dark state and a bright state. When switched to dark state, the optical gating absorbs substantially all of the transmitted radiation and when switched to bright state, the optical gating reflects substantially all transmitted radiation back to the sheet. This solution addresses the problem of measurement against different backings taking place in different areas of the web, but brings out other challenges, mainly in the form having simultaneously sufficient reflectivity and enough contrast between the two states, as well as the stability of the states.

Yet another method is presented in U.S. Pat. No. 5,793,486, where it is suggested to measure the white and black backings simultaneously. The measurement is done by using two spectrometers, where the first spectrometer measures the radiation reflecting from the paper upon the black backing and the second spectrometer measures the radiation reflecting from the paper upon the white backing. This solution also addresses the problem of measurement against different backings taking place in different areas of the web, but brings out other challenges: this method requires at least partially different optical paths for illuminating the web upon white and black backing and requires at least partially different optical paths for detecting the light from the web upon white and black backing and it requires two separate spectrometers. The complexity and cost of the measurement increases and for example the temperature stabilization becomes more challenging in harsh papermaking environment.

Also it is known to provide opacity compensated measurement of color of a moving web, by measuring the reflectance of the web over an opaque backing with specified reflectance properties and the transmittance of the web for opacity correction. This measuring principle is schematically shown in FIG. 1. A web 2, that travels in a machine direction indicated by an arrow A, has a first surface 2a and a second surface 2b. An on-line color measuring apparatus 1 includes a first sensor head 3 which is disposed adjacent the paper web surface 2a, above the web 2 and a second sensor head 4, which is disposed in close proximity of the paper web surface 2b, under the web. In sensor head 3 a light source 5 is arranged to illuminate the web surface 2a through a window 6. The light source 5 can be either a continuous lamp with or without a chopper or a flashing lamp. In sensor head 3, there is also a detector 7, such as a spectrometer for detecting the radiation entering the sensor head 3 through the measuring window 6. The second sensor head 4 is placed on the other side of the web, in fixed position relative to the sensor head 3. In sensor head 4, in close proximity of the web there is disposed a means 8 for providing an opaque backing for measuring the reflectance of the web 2. One example of a suitable backing means 8 is shown in FIG. 1a as an upper view. The backing means 8 is a round disc in which is arranged at least one opaque backing element 8a and at least one measurement window 8b having sufficient transmittance properties for transmittance measurements. Also an additional measurement window 8c having different transmittance properties and another opaque backing element 8d having different reflectance properties can be used in the measurement. Usually the opaque backing elements 8a, 8d are white or black in color and their transmittance is 0%. For transmittance measurement the opaque backing element is moved out of the illumination path and replaced with one of the measurement windows 8b, 8c by rotating the means 8. The means 8 can be for example a spinning wheel with at least an opaque backing area and a transparent area for transmittance measurement. For rotating and positioning the means 8 as required, there are electro-mechanical means in the sensor head 4 (not shown in the FIG. 1). When measuring the transmittance of the web, the radiation from light source 9 travels through the measuring window, the protection window 10 of the sensor head 4, the web 2 and the protection window 6 of the sensor head 4 to the detector 7. In both sensor heads 3 and 4, there are also filters and other equipment that have not been presented in FIG. 1 for clarity.

The drawback of using this measuring equipment is that a relatively slow electro-mechanical means is required to rotate and position the means 8. This means, that the reflectance and transmittance of the web are measured at different times and thus from different areas of the web. Usually the measurement is done by measuring reflectance and transmittance during separate scans resulting in considerable time delay between the measurements and thus poor opacity compensation.

BRIEF DESCRIPTION OF THE INVENTION

An objective of the invention is to provide a method and an apparatus for measuring the color of a moving web, wherein the above-mentioned problems are overcome.

The invention is based on the idea to use a backing element having specific translucent properties for opacity compensation for color measurement of a moving web. The radiation measured in the transmittance measurement is transmitted through the backing element. The backing element having specific translucent properties, i.e. sufficient reflectance and transmittance, makes it possible to measure the reflectance and the transmittance of the moving paper web essentially simultaneously and thus essentially from the same spot of the paper web.

According to one embodiment of the invention, the reflectance and transmittance are measured with a common viewing optics and a common detector located in the first sensor head on one side of the measured paper. Thus for measuring the transmittance of the web, the web is illuminated by radiation penetrating the backing before entering the web and passing through it to a detector. The light source is situated behind the web and the backing. The measuring configuration includes a first sensor head with detector and a light source and a second sensor head with a light source and a backing. The reflectance measurement is done by illuminating the web with the first light source and detecting the radiation reflected from the web with the detector. The transmittance measurement is done by illuminating the web with the second light source in the second sensor head, through the backing and detecting the radiation transmitted through the backing and the web. The changing of illumination between reflectance and transmittance measurement is preferably done in such a way that at least one of the light sources is pulsating, for example by using any number of flash lamps or LEDs (Light Emitting Diode), or by chopping the light from a continuous light source. In this way, the changing of illumination between measurements is quick and easy and provides a way to measure the transmittance and reflectance essentially on the same spot of the moving web.

According to another embodiment of the invention, only one light source is used for providing illumination for both reflection and transmittance measurement. The first sensor head includes a light source and a detector for the reflectance measurement, similarly as explained in the first embodiment. In the second sensor head, there is a second detector and a backing. For transmittance measurement, the radiation from the light source in the first sensor head is transmitted through the web and through the backing behind it, to the second detector in the second sensor head.

The backing element used in the measurement can be an element with locally specific translucent properties or it can be made of homogenous translucent material, e.g. Spectralon® (Spectralon® is a registered trademark of Labsphere inc.), which has good reflectance properties and also transmits sufficient amount of light for transmittance measurement. Such a backing can thus be used both in reflectance and transmittance measurements, without a need to move or replace the backing with another backing or measurement window between the measurements.

From the web measurements, opacity compensated color is defined with a Kubelka-Munk based algorithm. Modified Kubelka-Munk algorithm or an empirical, "best fit" algorithm or any other model can also be used.

The advantage of the invention is, that because there is no need to use any mechanical means for moving the backing, the reflectance and transmittance measurements can be made one after the other so fast, that they happen essentially simultaneously. Thus the opacity compensated measurement can be provided fast and essentially from the same spot of the moving web. In addition, because the measuring sensor does not have any moving parts for moving or replacing the backing with another backing or measurement window, the construction of the sensor is simplified, and the maintainability and reliability of the sensor increases.

BRIEF DESCRIPTION OF THE DRAWINGS

In the following, the present invention will be described in more detail with reference to the appended figures, in which

In FIGS. 2-7d corresponding numbers have been used for corresponding components and they have not been described separately, unless necessary for clarity.

DETAILED DESCRIPTION OF THE INVENTION

Figure 1:
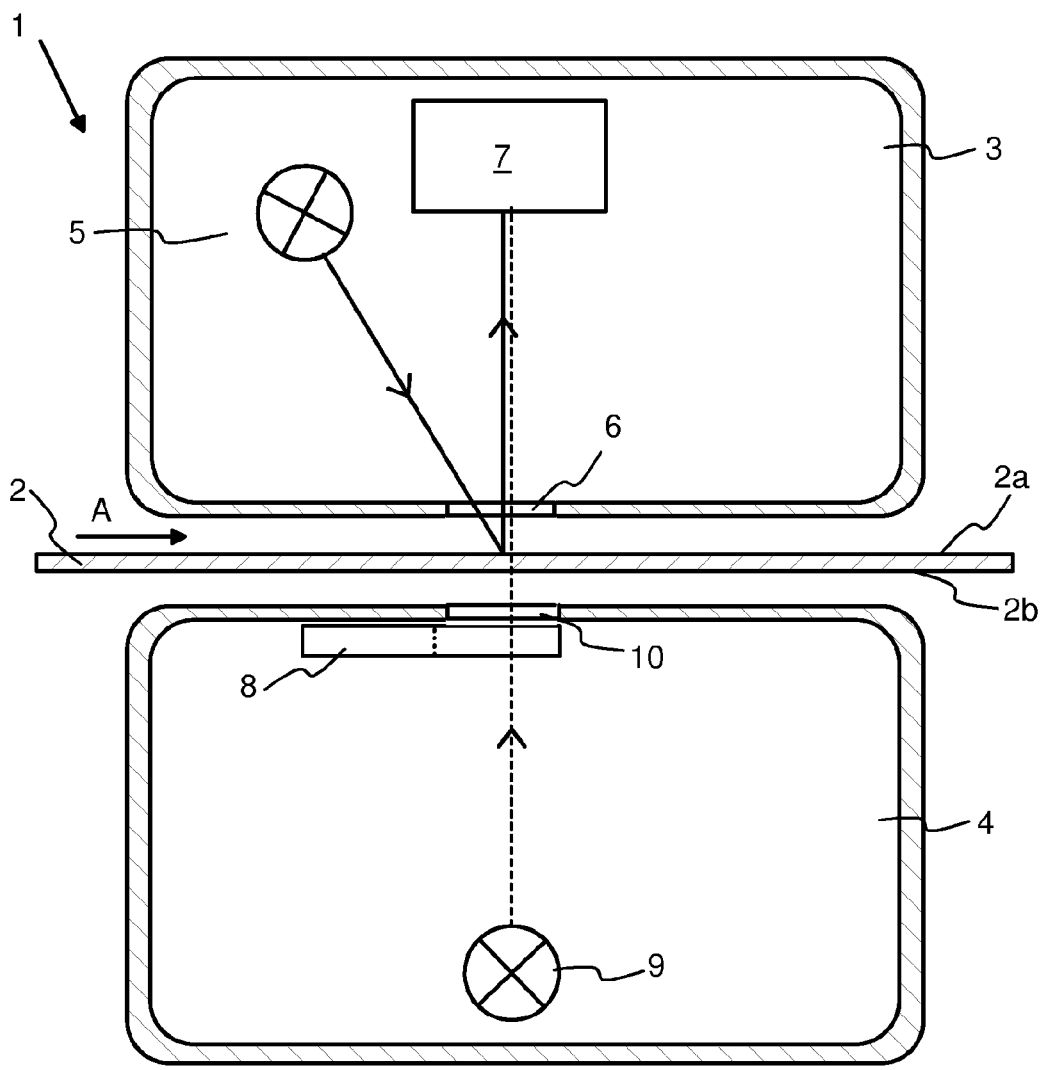
FIG. 1 shows a schematic, front elevation view of an on-line color measuring apparatus according to prior art.
Figure 1A:
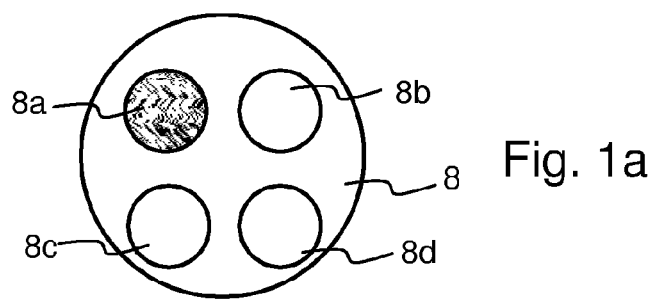
FIG. 1a shows an upper view of an backing means 8, that can be employed in prior art measuring apparatus of FIG. 1.

FIG. 1 and FIG. 1a have been explained above and thus they will not be discussed here any more.

Figure 2:
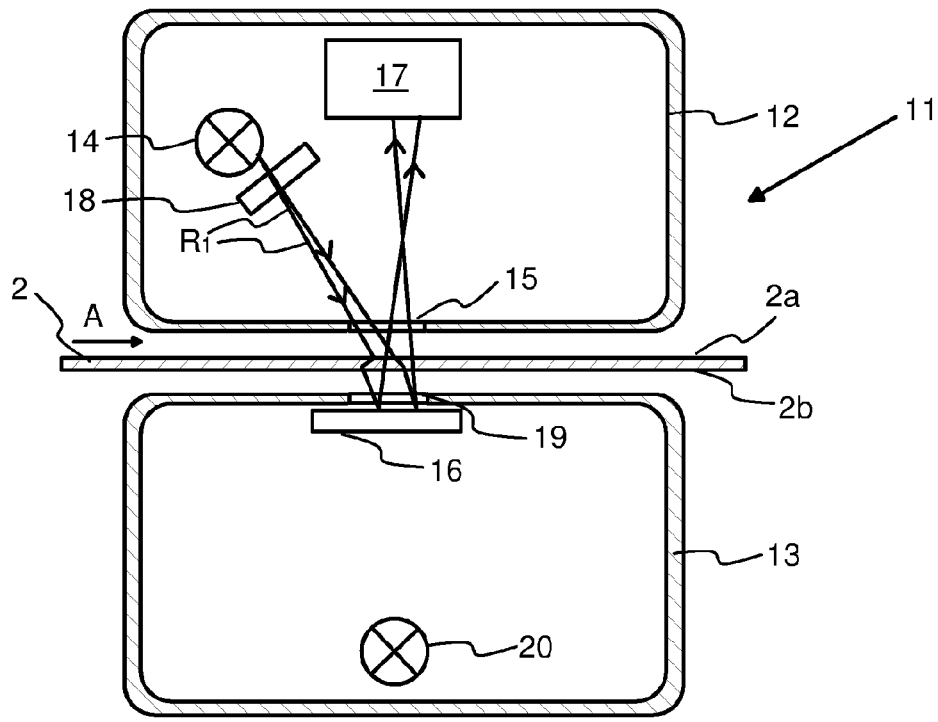
FIG. 2 shows a schematic, front elevation view, partly in section, of an on-line color measuring apparatus according to the invention, presenting reflectance measurement of the web.

FIG. 2 shows a schematic view of an on-line color measuring apparatus 11 according to the invention. The color sensor apparatus 11 includes a first sensor head 12 which is disposed adjacent to the upper paper web surface 2a, and a second sensor head 13, which is disposed in close proximity of the lower paper web surface 2b. The sensor heads 12 and 13 are set up in fixed position relative to each other in a measuring frame (not shown in figure) extending across the web or in a fixed point frame. The sensor apparatus 11 is shown in a state where the reflectance of the web 2 is being measured, showing the radiation $R_1$ of the light source 14 illuminating the web surface 2a through a protection sensor window 15. On the other side of the web, in sensor head 13, there is a backing 16 having required reflectance properties placed in close proximity of the web 2. The backing may be arranged in the sensor head 13 behind a protection window 19 or it may be placed in the sensor head to act as a window itself. The radiation reflected from the web 2 and also partially from the backing 16 and through the web 2 is detected by the detector 17. The light source 20 in the sensor head 13 is switched off during reflectance measurement, as depicted in FIG. 2. It is also possible that the light source 20 is not switched off, but it's effect is mathematically subtracted from the detected signal. The protection sensor windows 15 and 19 shown in this embodiment are not compulsory for the working of the sensors but they can be arranged in the sensor heads 12 and 13 if preferred. The backing element 16 is stationary and/or it can be situated in affixed position relative to at least one of the sensor heads 12, 13.

The light source 14 is preferably a UV rich Xenon lamp. It can be a pulsating light source or a continuous one. If required, it's spectral distribution can be modified or altered by a filter 18, for example, to produce the required distribution. It can include means for protection purposes, such as windows. The illumination may be arranged either as a direct illumination by a circumferential light ring, or as a diffuse one, or by other means. The detector 17 is disposed in the detector head 12 and it can also include means for protection purposes, such as windows.

Figure 3:
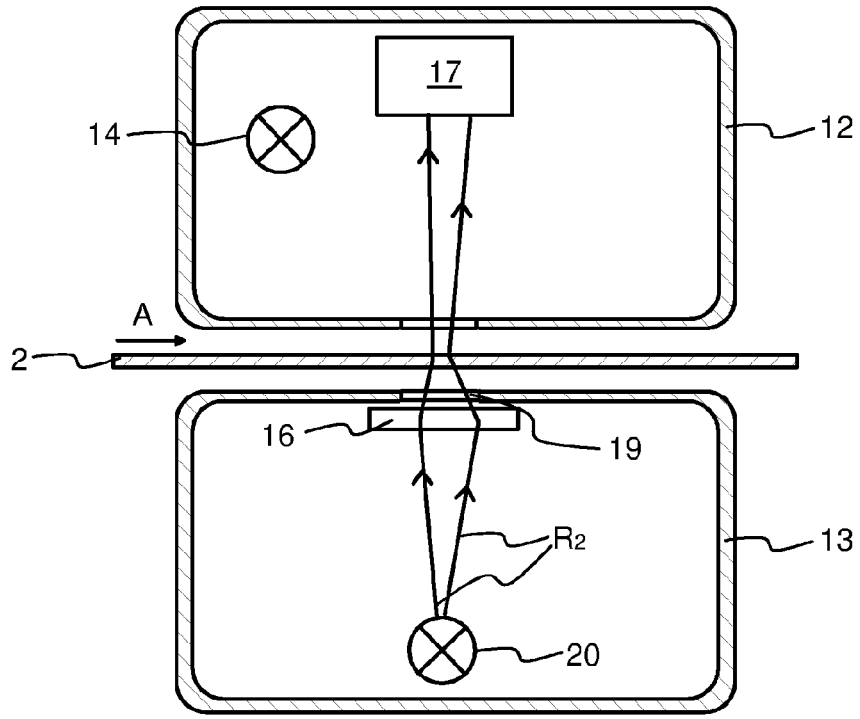
FIG. 3 shows the on-line color measuring apparatus of FIG. 2, presenting transmittance measurement of the web.

FIG. 3 shows the on-line color measuring apparatus of FIG. 2, when performing the transmittance measurement of the web. As it is illustrated in a simplified manner, the radiation $R_2$ of light source 20 illuminates the web 2 through the backing 16. The radiation $R_2$ travels through the backing 16, through the protection window 19 of the sensor head 13 and through the web 2 and is detected by the detector 17 in sensor head 12. When measuring the transmittance of the web, the light source 14 in the sensor head 12 is switched off. It is also possible that the light source 14 is not switched off but it's effect is mathematically subtracted from the detected signal. The light source 20 is preferably a LED. The light source 20 can be a pulsating light source or a continuous one. If required, its spectral distribution can be modified or altered to produce the required distribution.

The transmittance measurement is thus performed by through the same backing element 16 which is used as a backing in the reflectance measurement. The backing element is preferably stationary, i.e. solidly attached to the sensor head 13. Because the transmittance measurement is performed through the backing, there is no need for mechanical means for moving the backing out of the illumination path or, for replacing it with measurement window with required transmittance properties for transmittance measurement as is done in apparatuses according to the prior art. As can be derived from the above, the light sources 14 and 20 do not illuminate the web at the same time. At least one of them is at least partially switched on and off.

Figure 4:
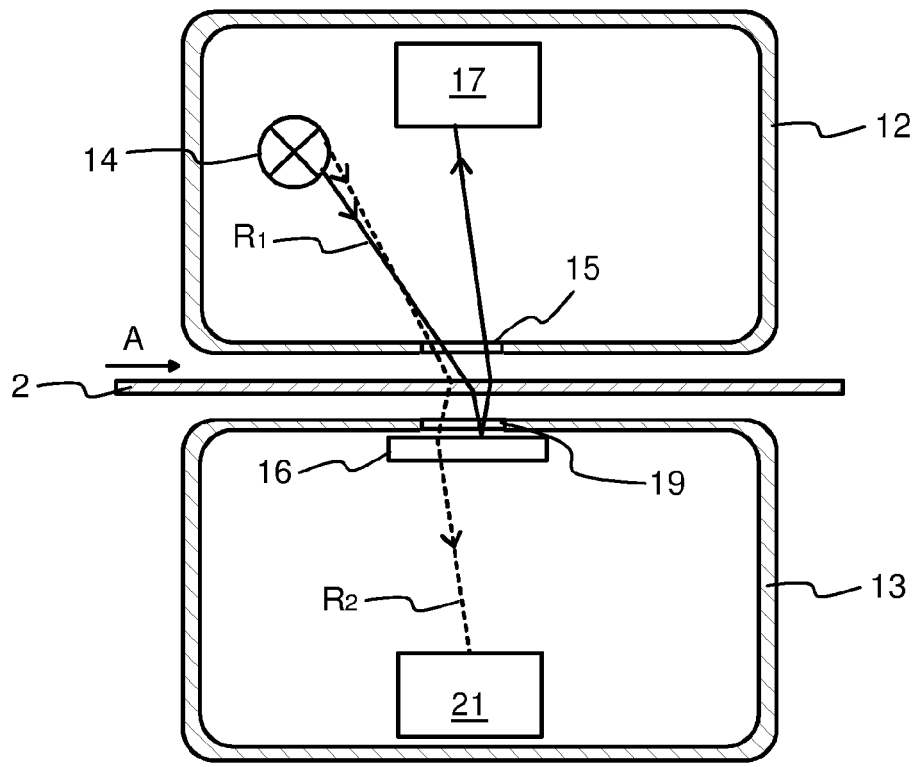
FIG. 4 shows a schematic, front elevation view, partly in section, of another on-line color measuring apparatus according to the invention.

In FIG. 4 is shown another embodiment of the invention, where the color measurement is realized by using only one light source and two detectors. In the first sensor head 12 there is, similarly to the embodiment shown in FIGS. 2 and 3, a light source 14 and a first detector 17 for the measurement of the reflectance of radiation R1. In sensor head 13, which is set up in fixed position relative to sensor head 12, there is disposed a second detector 21 and a backing 16. The reflectance measurement is performed accordingly with the embodiment described in connection with FIG. 2 and thus it will not be explained here. The transmittance measurement is accomplished by illuminating the web 2 with radiation from the light source 14 and detecting the radiation penetrated through the web 2 and backing 16 by the second detector 21. Accordingly, the transmittance measurement is done through the backing 16.

There are several alternatives for the material for the backing element. It is important, that the backing can both reflect and transmit sufficient amounts of radiation. Transmittance of the material is preferably above 10% and reflectance preferably above 80%. A preferred alternative for translucent backing is to use a suitable thickness of homogenous, white material, e.g. sintered Teflon powder, such as Spectralon®. Spectralon® is highly reflective and scattering and has sufficient transmittance for the measurement. A slice of Spectralon® of sufficient thickness can have reflectance of more than 85% and transmittance of more than 30%. Another example of a homogenous backing element is a white ground glass plate.

Figure 5A:
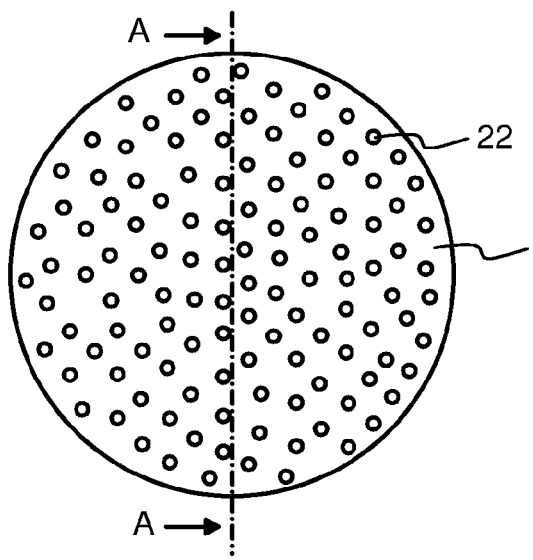
FIG. 5a shows an upper view of one suitable backing, that can be used in the on-line color measuring apparatus according to the invention.
Figure 5B:
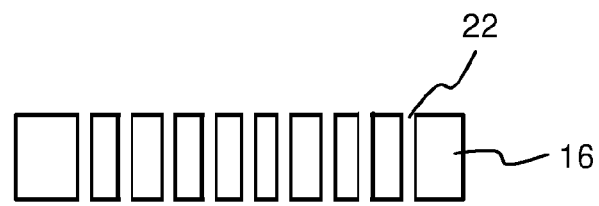
FIG. 5b shows a cross sectional view along line A-A of FIG. 5a, FIG. 6a shows an upper view of another suitable backing, that can be used in the on-line color measuring apparatus according to the invention.
Figure 6A:
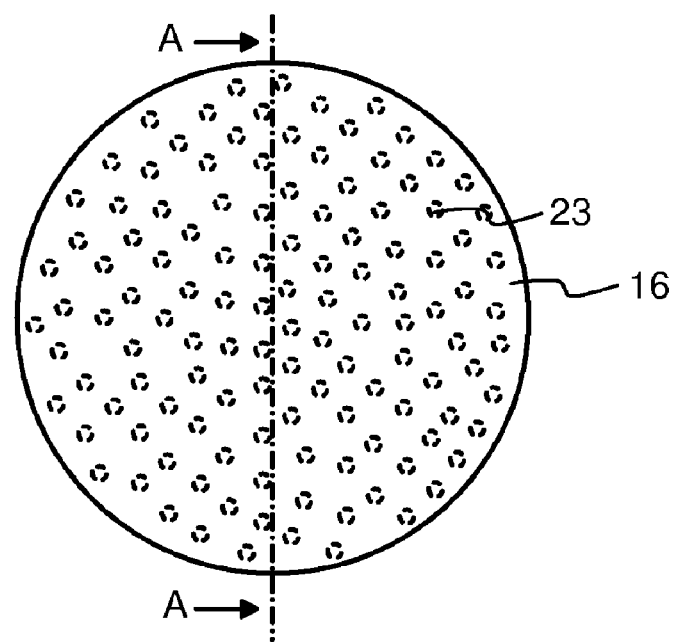
Figure 6B:
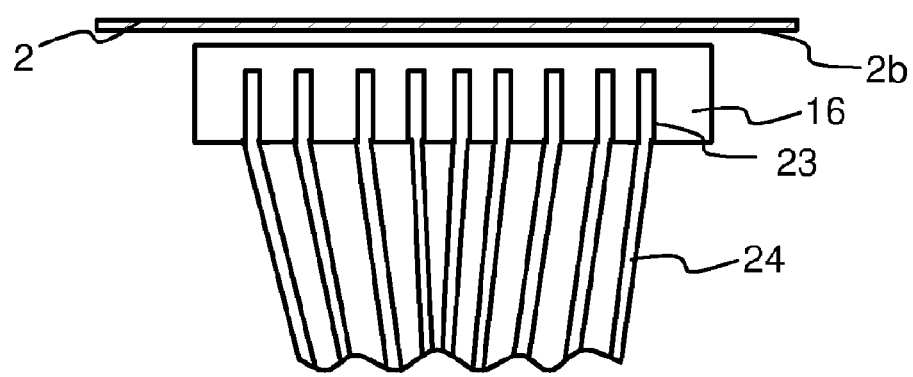
FIG. 6b shows a cross sectional view along line A-A of FIG. 6a, FIG. 7a shows a front elevation view of another suitable backing, that can be used in the on-line color measuring apparatus according to the invention.

Another possibility is to use a backing, that has locally specific transmittance properties. One option to get the locally specific properties is to drill required amount of holes of any size in or through the backing material. This embodiment of the backing is shown in FIGS. 5a and 5b. FIG. 5a shows an upper view of one backing element 16, that has holes 22 drilled in it. FIG. 5b shows a cross sectional view A-A of FIG. 5a. The holes expand at least partially through the element and preferably their diameter is small to assure a good spatial uniformity. The number of holes is large enough to assure that the transmittance of the backing is high enough, but small enough to assure, that the reflectance of the backing is high enough. In this embodiment, transmittance of the backing material itself is preferably about 0% while the reflectance is high. Also translucent materials, such as Spectralon® can be used, on condition that required level of transmittance is achieved Another possibility to get the locally specific transmittance properties is to use a backing element with optical fibers attached to it for providing the transmittance illumination. FIG. 6a shows an upper view of such backing element 16, and FIG. 6b shows a cross sectional view A-A of FIG. 6a. As can be realized from the FIG. 6b, the backing 16 has perforations 23 drilled in it for inserting the optical fibers into the backing. The perforations 23 do not necessarily penetrate the backing 16, but extend only a certain length into the backing 16. Thus the surface of the backing element, that is adjacent to the paper web surface 2b remains intact, smooth and whole. An optical fiber 24 is inserted into each perforation 23, to provide the illumination for transmittance measurement of the web. On their other ends the optical fibers are coupled to a light source or to the detector (these are not shown in the figures). In this embodiment, the transmittance of the backing material itself is preferably about 0%, while the reflectance is high. Also translucent materials, such as Spectralon® can be used, on condition that required level of transmittance is achieved.

Also its is possible to use other materials with locally specific translucent properties as a backing element. For any kind of backings, the color of the backing is preferably white, but backings of any other color can also be used. In the embodiments presented in this specification, the backing element has been shown to be round in shape, but any other shapes, e.g. rectangular or square, are suitable for the backing element. The choice of the element's shape can be made according to the requirements for the measurement device.

Figure 7A:
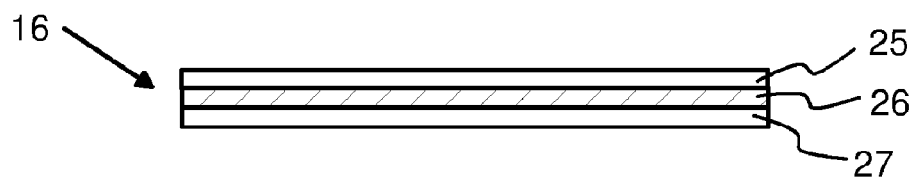

The backing element can also be comprised of several different materials attached to each other. Optionally, optical properties of one or more of these materials can be electrically changeable. In FIGS. 7a-7d are shown some examples of suitable backing elements of this kind. In FIG. 7a the backing element 16 is formed of three thin layers 25, 26, 27 of different materials that are attached to each other for example by glueing. The materials of the layers are selected in a way, that the backing element formed of them fulfils the simultaneous requirements for transmittance and reflectance, for example reflectance of about 80% and transmittance of about 10%. The backing is used in the measurements similarly to embodiments described in connection with FIGS. 2-4.

Figure 7B:
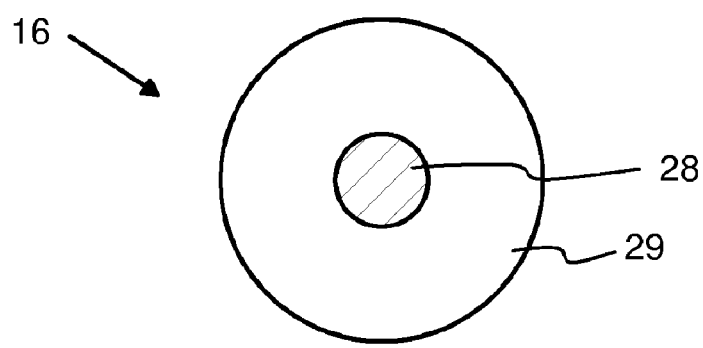
FIGS. 7b-7d show an upper view of three different backings, that can be used in the on-line color measuring apparatus according to the invention.

In FIG. 7b the backing element 16 is formed of two materials: translucent material and opaque material. In this embodiment, in the middle of the translucent material 29, e.g. glass, is attached a piece of opaque material 28. The measurement is conducted by directing the illuminations in different illumination states in a way that the reflectance measurement is conducted against the opaque material, i.e. against piece 28 and the transmittance measurement is done by illuminating the web through the translucent material 29.

Figure 7C:
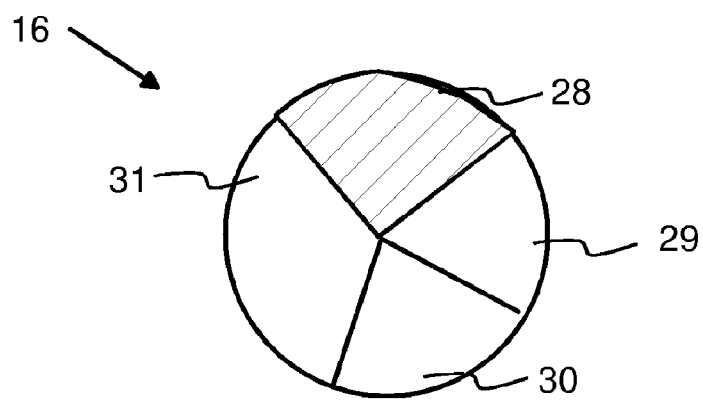

The backing element 16 can also be formed by attaching different materials together in the same plane as shown in FIG. 7c. The sector 28 is made from opaque material for reflectance measurement and one of the sectors 29, 30 or 31 are made from translucent material for transmittance measurements.

Figure 7D:
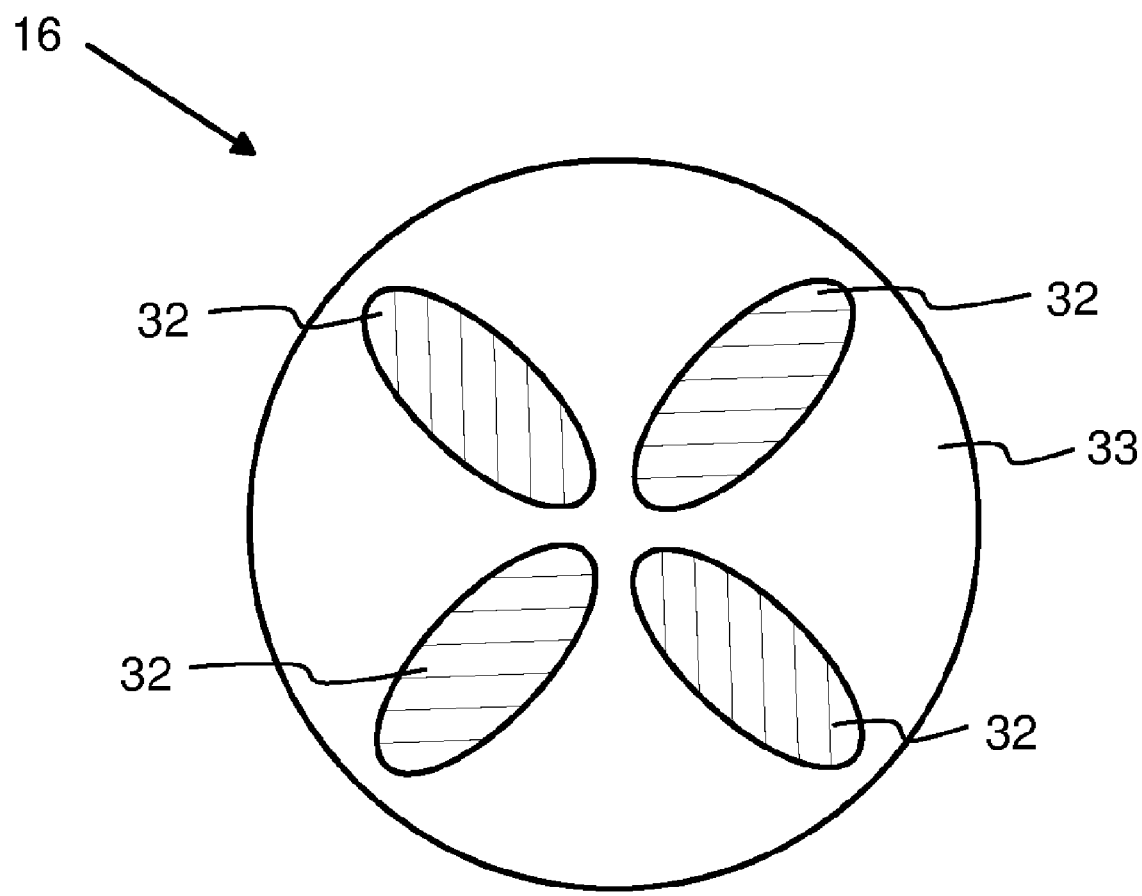

FIG. 7d presents another suitable backing element 16 for the measurement. The backing element 16 is made from material with high transmittance, e.g. glass, with opaque areas 32 formed in it. The areas 32 are formed by treating, e.g. grinding the surface. Another embodiment of a backing element 16 is to use an opaque backing material with high reflectance properties for the disc 33 itself and have holes drilled through the material outside the areas 32. In this embodiment, the transmittance of the backing material itself is preferably about 0% while the reflectance is high. Also translucent materials, such as Spectralon® can be used, on condition, that required level of transmittance is achieved.

The intention is not to restrict the invention to the embodiments described above by way of example, but it is intended that the invention can be interpreted widely within the scope of protection defined by the claims presented hereinbelow. Accordingly, the sensor heads of the color sensor apparatus can be arranged the other way round than presented in FIGS. 2 and 3. Thus first sensor head that is the sensor head 12 with the detector 17, can also be arranged under the web 2.

The invention claimed is:

1. A method for measuring color of a moving web, in which method the web is measured by reflectance measurement and transmittance measurement, wherein
   the reflectance measurement is carried out by illuminating a surface of the web in a measuring area, where on the other side of the web at the measuring area resides a backing element, and measuring the radiation reflecting from the web,
   the transmittance measurement is carried out by illuminating the web and measuring the radiation transmitted through the web,
   the radiation reflecting from the web in the reflectance measurement and the radiation transmitting through the web in the transmittance measurement are measured with the same detector, and the radiation measured in the transmittance measurement is transmitted through the backing element.

2. A method according to claim 1, wherein the backing element is stationary and/or in a fixed position relative to at least one sensor head.

3. A method according to claim 1, wherein in transmittance measurement the radiation to be measured is first transmitted through the backing element and then through the web.

4. A method according to claim 1, wherein the web is illuminated sequentially for reflectance measurement and/or transmittance measurement.

5. A method according to claim 1, wherein the reflectance measurement is carried out by measuring equipment arranged in a sensor head which is arranged on one side of the web and the backing element is stationarily fixed to a sensor head residing on the other side of the web.

6. A method according to claim 1, wherein, in the reflectance measurement and in the transmittance measurement, the same backing element is used.

7. A method according to claim 6, wherein the radiation measured in the transmittance measurement is transmitted through the backing element which is a translucent element with solid surfaces.

8. A method according to claim 6, wherein the radiation measured in the transmittance measurement is transmitted through the backing element which has holes at least partially penetrating it.

9. A method according to claim 6, wherein the radiation measured in the transmittance measurement is transmitted through the backing element which has perforations arranged in it, which perforations extend into the backing element leaving the backing element surface adjacent the web surface whole.

10. A method according to claim 9, wherein in the transmittance measurement the web is illuminated by optical fibers arranged in the perforations in the backing element.

11. A method according to claim 6, wherein the radiation measured in the transmittance measurement is transmitted through the backing element which comprises several different materials.

12. An apparatus for measuring the color of a moving web, which apparatus is arranged to measure the web by means of reflectance measurement and transmittance measurement, and in which apparatus for reflectance measurement there is at least
- a first light source that illuminates a surface of the web in the measuring area of the web,
- a backing element in the measuring area of the web on the opposite side of the surface of the web, and
- a detector for measuring the radiation reflected from the web, and for transmittance measurement there is at least
- a second light source for illuminating the opposite side of the surface of the web and
- a detector for measuring the radiation passed through the web, wherein
the same detector is arranged to measure both the radiation reflecting from the web in the reflectance measurement and the radiation transmitting through the web in the transmittance measurement and
in the transmittance measurement the detector is arranged to measure radiation that has passed through the backing element.

13. An apparatus according to claim 12, wherein the backing element is stationary, and/or in a fixed position relative to at least one sensor head.

14. An apparatus according to claim 12, wherein, in the transmittance measurement, the light source and the backing element are arranged on the same side of the web and the radiation is first transmitted through the backing element and then through the web before entering the detector.

15. An apparatus according to claim 12, wherein the first and second light sources are arranged to illuminate the web sequentially.

16. An apparatus according to claim 12, wherein the apparatus comprises two sensor heads, a first sensor head arranged on one side of the web, comprising at least a light source and a detector and a second sensor head, arranged on an other side of the web comprising at least the backing element.

17. An apparatus according to claim 16, wherein the second sensor head comprises a light source.

18. An apparatus according to claim 12, wherein the apparatus is arranged to use, in the reflectance measurement and in the transmittance measurement, the same backing element.

19. An apparatus according to claim 12, wherein the backing element is a translucent element with solid surfaces.

20. An apparatus according to claim 12, wherein the backing element has holes at least partially penetrating it.

21. An apparatus according to claim 12, wherein the backing element has perforations arranged in it, which perforations extend into the backing element leaving the backing element surface adjacent the web surface whole.

22. An apparatus according to claim 21, wherein there are optical fibers arranged in the perforations in the backing element.

23. An apparatus according to claim 12, wherein the backing element comprises of several different materials.

* * * * *